United States Patent [19]
Kushion

[11] Patent Number: 5,708,585
[45] Date of Patent: Jan. 13, 1998

[54] COMBUSTIBLE GAS MEASUREMENT

[75] Inventor: Mark Dennis Kushion, Saginaw, Mich.

[73] Assignee: General Motors Corporation, Detroit, Mich.

[21] Appl. No.: 407,351

[22] Filed: Mar. 20, 1995

[51] Int. Cl.[6] .................. G01F 1/68; G01N 25/22; G01N 25/30

[52] U.S. Cl. .................. 364/431.061; 364/431.062; 364/483; 73/204.14; 422/51; 422/95; 422/98; 436/147

[58] Field of Search .................. 364/431.06, 431.05, 364/483, 557, 558, 565, 431.061, 431.062; 73/118.1, 23.32, 23.31, 25.01, 25.03, 204.15, 204.14, 204.19, 204.25; 123/697, 688, 703; 422/94, 51, 95, 96, 97, 98; 374/36, 33, 40, 42; 436/141, 147

[56] References Cited

U.S. PATENT DOCUMENTS

| | | | |
|---|---|---|---|
| 4,329,874 | 5/1982 | Maeda | 374/36 |
| 4,512,313 | 4/1985 | Tsuchida et al. | 123/688 |
| 4,713,765 | 12/1987 | Abe et al. | 364/431.05 |
| 4,870,025 | 9/1989 | Hurley et al. | 436/141 |
| 5,265,417 | 11/1993 | Visser et al. | 60/274 |
| 5,360,266 | 11/1994 | Lenfers et al. | 374/36 |
| 5,444,976 | 8/1995 | Gonze et al. | 60/274 |
| 5,451,371 | 9/1995 | Zanini-Fisher et al. | 422/51 |
| 5,513,522 | 5/1996 | Seki et al. | 73/118.1 |

OTHER PUBLICATIONS

"A Thick-Film Calorimetric Sensor for Monitoring the Concentration of Combustible Gases", Sensor and Actuators, 19 (1989) 237-248 (month is not available).

"Planar type of carrier catalytic methane sensor", Sensors and Actuators B, 12 (1993) 19-23 (month is not available).

*Primary Examiner*—Kevin J. Teska
*Assistant Examiner*—Tan Nguyen
*Attorney, Agent, or Firm*—Michael J. Bridges

[57] ABSTRACT

A pulsed measurement technique for calorimetric sensors provides a short current pulse through catalyzed and inert sensor elements to minimize self heating while providing for sensor resistance measurement, so that a determination of the level of catalytic activity at the surface of the catalyzed element may be made for sensing the concentration of combustible elements of automotive internal combustion engine exhaust gas. Exhaust gas temperature measurement is provided by monitoring the inert element resistance. Exhaust gas flow rate measurement is provided by heating the inert element for a short heating period, and then removing the heat source while monitoring the time rate of return to the known initial inert element temperature.

12 Claims, 4 Drawing Sheets

COMBUSTIBLE GAS MEASUREMENT

FIELD OF THE INVENTION

This invention relates to measuring combustible gasses and, more particularly, to measuring the concentration of automotive internal combustion engine exhaust gas constituent elements using calorimetric sensors.

BACKGROUND OF THE INVENTION

Calorimetric sensors are known for sensing concentration of combustible industrial emissions. Such sensors typically include a plurality of closely matched temperature sensitive elements disposed in a path of flow of industrial emissions. At least one of the elements is coated with a catalyzed element. As the industrial emissions flow over the sensor elements, exothermic oxidation of any combustible elements in the emissions may occur at the surface of the catalyzed elements increasing the temperature of the catalyzed elements over that of the inert (noncatalyzed) elements. The temperature difference may be measured as a difference in electrical resistance across the elements and is proportional to combustible gas concentration.

The temperature Tnc of non-catalyzed calorimetric sensor elements may be expressed as $$Tnc=(Qe/hAsnc)+Tg$$

in which Qe is the electrical power supplied to the element, hAsnc represents the heat transfer properties of the non-catalyzed element, and Tg is exhaust gas temperature. The temperature Tc of catalyzed calorimetric sensor elements may be expressed as $$Tc=((Qe+Qcat)/hAsc)+Tg$$

in which Qcat is the energy provided by the exothermic oxidation reaction at the surface of the active catalyzed sensor element, and hAsc represents the heat transfer properties of the catalyzed sensor element. The temperature difference, which indicates the level of oxidation activity at the surface of the catalyzed element, may therefore be expressed in simplified form as $$\Delta T=(Qcat/hAsc)+(Qe/hAsc)-(Qe/hAsnc).$$

To elevate the temperature of the catalyzed elements to light-off and to stabilize the heat transfer properties of the sensor elements by maintaining substantially constant element temperature so as to minimize sensor error, the sensor elements are typically self-heated, wherein during sensor operation, a small dc current is passed through each of the elements. Self-heated elements require substantially matched heat transfer properties between the catalyzed and the inert elements in order to have sensor output be a function of the catalyzed element and the catalytic reaction. Specifically, the temperature difference for the self-heated elements may be expressed as follows $$\Delta T=(Qcat/hAsc)+(Qe/hAsc)-(Qe/hAsnc)$$

in which hAsc and hAsnc both vary with exhaust gas flow rate, exhaust gas temperature and sensor element surface area. For proper calorimetric self-heated sensor operation at a variety of stable temperatures, the heat transfer properties hAsc and hAsnc must be matched closely.

It would be desirable to apply the accurate yet inexpensive calorimetric sensors in automotive vehicle internal combustion engine exhaust gas analysis applications, which require accurate emissions concentration sensing at minimum cost. However, current sensor implementations are not suited to the task. For example, automotive internal combustion engine exhaust gas temperature and flow rate vary significantly and unpredictably. Further, the surface area of typical calorimetric sensor elements may vary substantially from element to element. Only through added expense or complexity can the flow rate or temperature of automotive engine exhaust gas be sufficiently stabilized or the element to element surface area variability of calorimetric sensor elements be sufficiently reduced to increase the correlation in heat transfer properties between the sensor elements. Accordingly, it may be difficult or expensive to achieve an acceptable degree of accuracy in automotive internal combustion engine exhaust gas measurement with conventional calorimetric sensor approaches.

SUMMARY OF THE INVENTION

The present invention overcomes the limitations of the prior art through a pulsed measurement technique for calorimetric sensors. Such technique eliminates sensor self-heating, reducing calorimetric sensor sensitivity to variations in exhaust gas flow rate, exhaust gas temperature, or sensor element surface area.

More specifically, in automotive internal combustion engine applications, the engine exhaust gas temperature is sufficient to support light-off of catalyzed sensor elements, so external supplemental heating is unnecessary to keep the catalyzed element catalytically active. A voltage pulse is applied across the catalyzed and inert elements to provide for a reading of the element resistance. The pulse is of sufficiently short duration that the energy transferred to the elements is insufficient to provide any significant self-heating of the elements. Convective losses are thereby theoretically eliminated from the elements since the surface temperature is substantially equal to the engine exhaust gas temperature. The sensor output, based on the temperature difference between the elements therefore is then a function of the catalytic action and the heat transfer properties of the catalyzed element only. More specifically, for the pulsed measurement approach of the present invention, the temperature difference between the sensor elements is, as described $$\Delta T=(Qcat/hAsc)+(Qe/hAsc)-(Qe/hAsnc),$$

in which Qe may be expressed as $$Qe=I^2 * R * t$$

in which I is the current through the element, R is the element resistance, and t is the time duration of the current pulse applied to the sensor elements under the pulsed measurement approach of this invention. By reducing the time t toward zero in accord with an important feature of this invention, Qe is reduced toward zero and, in any case, for practical applications in accord with this invention, Qe<<Qcat, such that $$Tnc \approx Tg$$

and $$Tc=(Qcat/hAsc)+Tg,$$

so that the temperature difference reduces to $$\Delta T=Qcat/hAsc,$$

indicating that the temperature difference under the pulsed approach of the present invention is independent of the heat transfer characteristics of the non-catalyzed element, eliminating the requirement of precise matching of the heat transfer characteristics, providing for robust sensing of combustible elements in internal combustion engine exhaust gas.

In accord with a further aspect of this invention, the short duration pulse applied to the inert (or non-catalyzed) element or elements provides for an accurate measurement of exhaust gas temperature. Further, the measured temperature may then be used to compensate for any calibrated temperature change-based variations in the heat transfer properties of the elements. Still further, the measured temperature may be used for diagnostic monitoring of exhaust system components.

In accord with yet a further aspect of this invention, the inert element or elements may be used for measuring engine exhaust gas flow rate and the flow rate used to compensate for any flow rate-based variations in heat transfer properties of the elements. The flow rate may be measured through a short period of self-heating of the inert element or elements and an analysis of the heat transfer provided by the engine exhaust gas passing across the element. For a given exhaust gas temperature that may initially be measured, a direct, calibratable relationship exists between exhaust gas flow rate and change in temperature of the element away from the self-heating temperature. When the flow rate measurement is complete, the self-heating may be discontinued so that a measurement pulse may be applied to the inert element or elements soon thereafter for concentration measurement in accord with this invention. A heat transfer property correction value may be then be referenced from a stored schedule using the measured flow rate, and the correction value applied in the determination of the concentration values.

BRIEF DESCRIPTION OF THE DRAWINGS

The invention may be best understood by reference to the preferred embodiment and to the drawings in which.

DESCRIPTION OF THE PREFERRED EMBODIMENT

Figure 1:
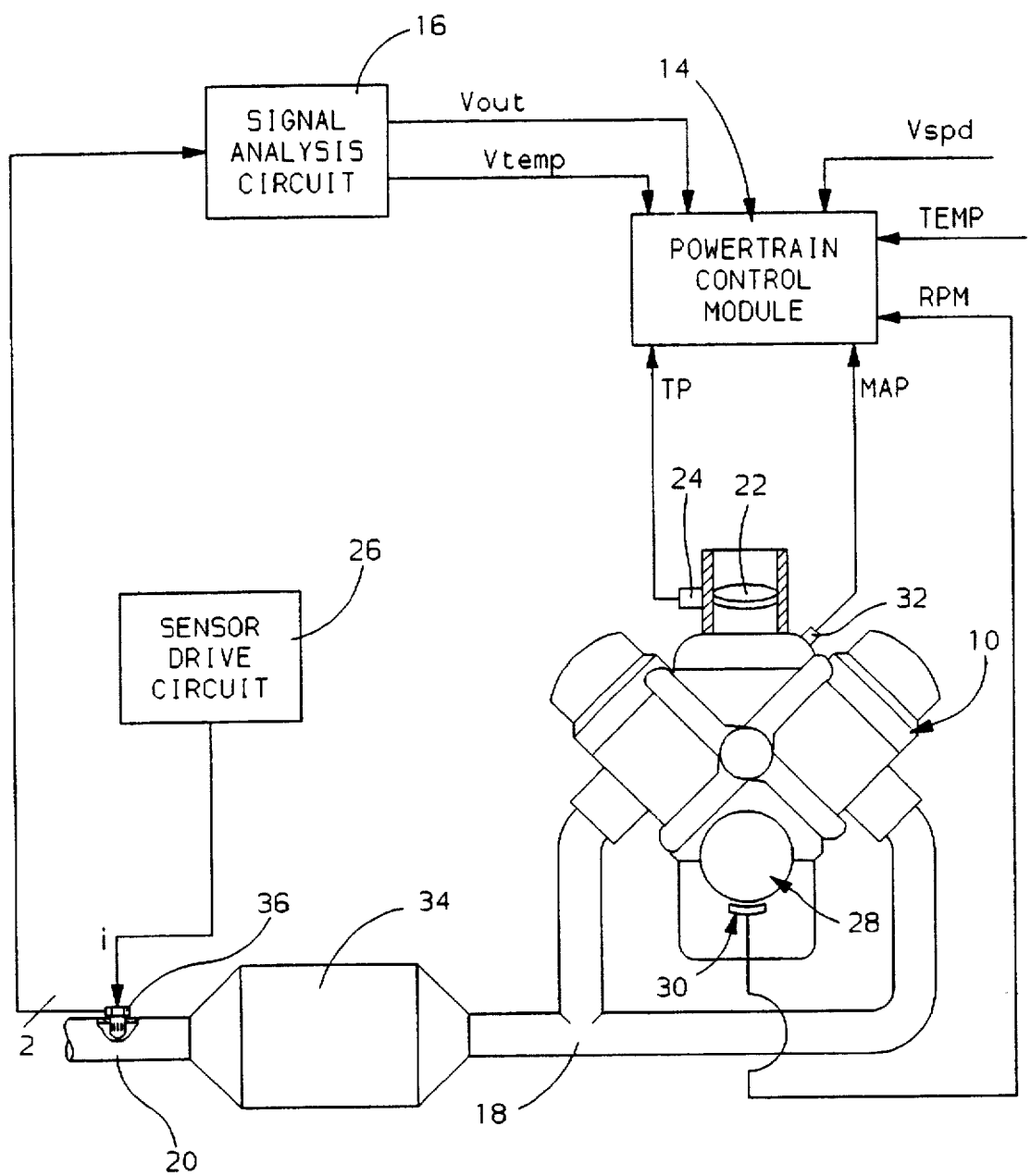
FIG. 1 diagrams the calorimetric sensor hardware used for engine exhaust gas concentration measurement in accord with a preferred embodiment of this invention.

Referring to FIG. 1, an internal combustion engine 10 receives inlet air through positioning of conventional inlet air valve 22, such as a butterfly or rotary valve, the position of which is transduced by conventional inlet air valve position sensor 24 outputting a representative position signal TP. The inlet air is received into an intake manifold (not shown) of the engine 10, and the absolute air pressure in such intake manifold is transduced by conventional pressure transducer, 32 outputting a signal MAP indicating manifold absolute air pressure MAP. The inlet air is combusted in the engine cylinders (not shown) and the combustion waste product in the form of exhaust gas is guided out of the engine cylinders and through exhaust gas conduit 18 to catalytic treatment means 34 for catalytic treatment therein. The catalytically treated exhaust gas exists to the atmosphere via exhaust gas outlet conduit 20. A conventional calorimetric sensor 36 is disposed in the exhaust gas outlet conduit 20 to sense concentration of at least the combustible exhaust gas constituent elements of carbon monoxide CO and hydrocarbon HC. The sensor 36 outputs signal information indicating such concentration to signal analysis circuit 16. A sensor drive circuit 26 is provided in a critical feature of this invention for providing a drive signal i in the form of a pulsed sensor drive current signal to the sensor 36 for energizing the sensor so that the sensor output signals may be produced, ultimately for analysis by the signal analysis circuit 16. Through the operation of the signal analysis circuit 16, to be described, an output signal Vout, indicating the concentration levels of at least CO and HC, is output and a signal Vtemp, indicating exhaust gas temperature, is output. The specific features of the sensor 36, the sensor drive circuit 26 and the signal analysis circuit 16 will be further described.

A powertrain control module PCM 14 includes such generally-known elements as a microcontroller having a central processing unit including conventional arithmetic logic circuitry for carrying out mathematical functions, a read only memory ROM or a non-volatile memory unit for storing calibration values and calibration schedules and tables, random access memory RAM, extended memory and input/output circuitry. The PCM 14 is provided for reading the input signals including the described MAP signal, TP signal, the Vout and Vtemp signals, and further input signals generally understood in the art to be required for conventional powertrain control operations. For example, such further signals may include a signal Vspd, indicating automotive vehicle speed, a signal TEMP, indicating engine coolant temperature, and a signal RPM indicating the angular rate of rotation of an engine output shaft 28 such as an engine crankshaft. Such engine output shaft is rotated through the combustion force generated during engine combustion events in a well-known manner. Teeth or notches may be located about the circumference of a portion of the output shaft 28 and a conventional hall effect or variable reluctance sensor 30 positioned to sense passage of the teeth or notches by a fixed position relative to the output shaft 28. The sensor 30 outputs a periodic signal having a frequency proportional to the rate of rotation of the output shaft 28.

The PCM 14 carries out conventional powertrain control, diagnostics and maintenance functions while operating, such as while an automotive vehicle operator applies ignition power to the PCM 14 through manual positioning of a conventional ignition switch to an "on" position. In the execution of such PCM 14 functions, the series of described sensor signals may be periodically read and a series of control and diagnostic signals generated for application to control actuators or to diagnostic indicators. The functions may be carried out by executing, in a step by step manner while the PCM 14 is operating, a series of processor instructions stored in PCM non-volatile memory.

Figure 2:
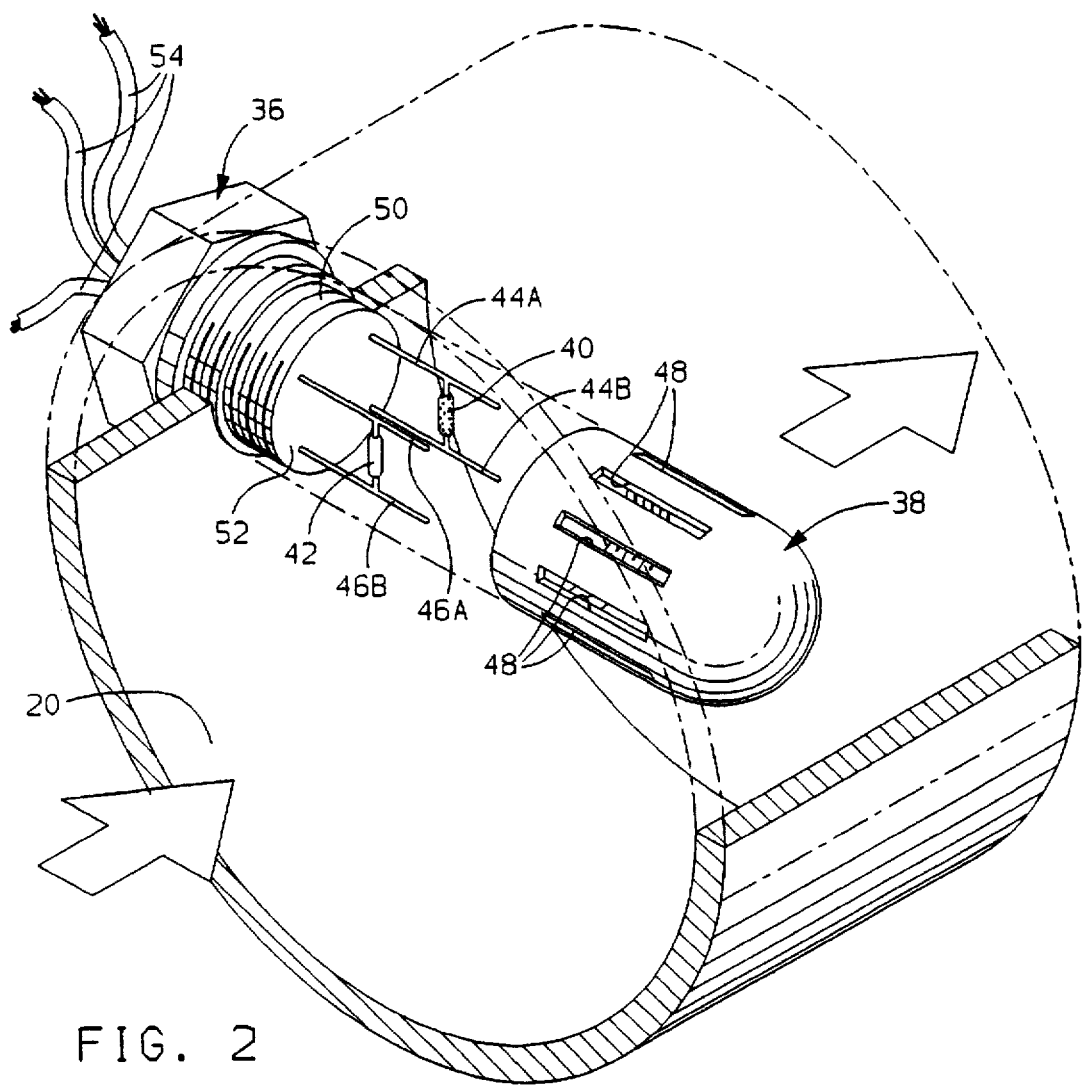
FIG. 2 illustrates typical calorimetric sensor positioned in a path of flow of internal combustion engine exhaust gas.

Referring to FIG. 2, the conventional calorimetric sensor 36 of this embodiment is further detailed. The sensor 36 is fixedly positioned on the conduit 20 so that sensor body 52 passes through the conduit wall and into the path of flow of engine exhaust gas passing through the conduit 20. The sensor body 52 includes an outer threaded portion 50 providing for threadable engagement of the sensor 36 with the conduit 20.

Two closely meshed temperature sensitive elements 40 and 42 are provided for sensing engine exhaust gas concentration and exhaust gas temperature in accord with this invention. The elements 40 and 42 are comprised of substantially identical platinum heater/resistance thermometer films fabricated by a thick film metallization process. Both elements are washcoated and then, in accord with general principals of calorimetric sensor design, one sensor element 40 is coated with a catalyst, such as platinum black or palladium, which may be deposited either chemically or electrolytically on the platinum film of the sensor element 40. The non-catalyzed element 42 glass-sealed so that no oxidation reaction occurs at its surface, so that it may be used simply for engine exhaust gas temperature sensing, such as to provide a reference temperature to which the temperature of the catalyzed element 40 may be compared. Electrically conductive legs 44a and 44b extend outward from the sensor body 52 substantially along the conduit 20 diameter. Catalyzed element 40 is positioned between the legs 44a and 44b away from the wall of conduit 20 so as to be exposed to engine exhaust gas passing through conduit 20. Likewise, electrically conductive legs 46a and 46b extend outward from the sensor body 52 substantially along the conduit 20 diameter and substantially in parallel with sensor legs 44a and 44b. Noncatalyzed element 42 is positioned between the legs 46a and 46b away from the wall of conduit 20 so as to be exposed to engine exhaust gas passing through conduit 20.

Generally, due to the absence of external heating of the sensing elements 40 and 42 in accord with a critical feature of this invention, any temperature rise in the catalyzed element 40 over the temperature of the noncatalyzed element 42 is attributable to energy transferred by the exothermic oxidation reaction of the catalyst and combustible engine exhaust gas constituent elements of CO and HC incident thereon. As is generally understood in the calorimetric sensor art, the heat energy transferred by the oxidation reaction is substantially proportional to the concentration of CO and, under high temperature conditions, HC in the engine exhaust gas. To measure and monitor such resistance values, the electrically conductive legs 44a, 44b, 46a and 46b are accessed electrically by the series of conductors 54. In this embodiment, a controlled drive current i is applied from a predetermined one of the conductors 54 to the conductive leg 44a, through the catalyzed sensing element 40 and along conductive leg 44b. Conductive legs 44b and 46a are electrically shorted together, providing for the passage of the drive current i along conductive leg and through the noncatalyzed sensing element 42. The drive current then returns through conductive leg 46b to a predetermined one of the conductors 54 to a ground reference. A predetermined one of the conductors 54 is electrically connected to the connection between legs 44b and 46a, so that information on the voltage at such connection may be made available. The electrical connection of the conductive legs and the conductors 54 will be further detailed. Hollow shell 38 is sized to fit over the sensing element 40 and 42, and may be threadably engaged with the sensor body 52 via the threaded portion 50. The shell 38 provides a protective covering over the elements 40 and 42, yet allows passage of a representative portion of engine exhaust gas by the sensing elements 40 and 42 via passages or slots 48 in the shell 38. Accordingly, as engine exhaust gas passes through the slots or openings 48 the concentration of the elements HC and CO may be sensed as a difference in temperature or equivalently a difference in resistance across the elements 40 and 42.

Figure 3:
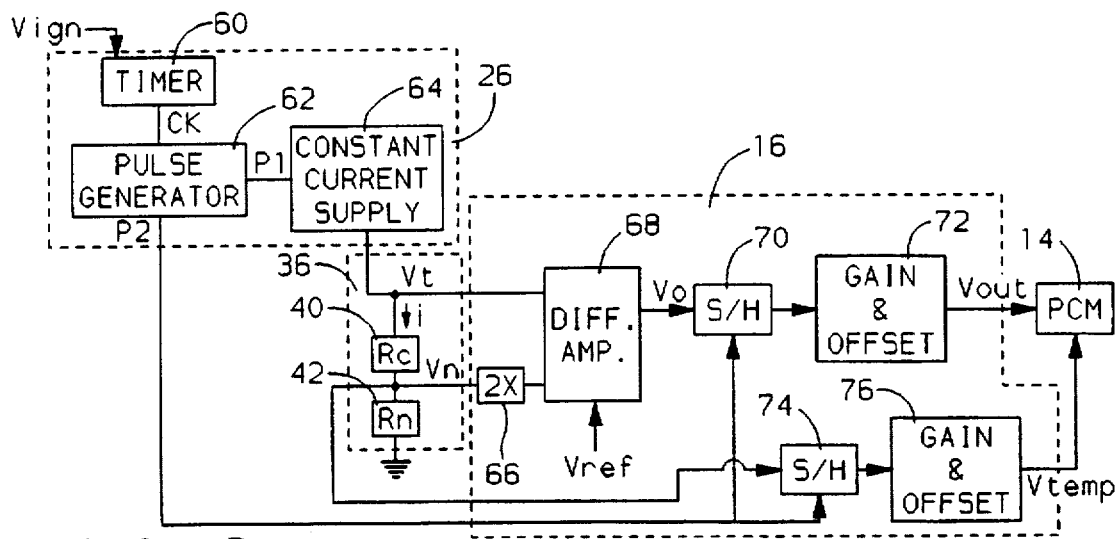
FIG. 3 describes circuitry for energizing the calorimetric sensor of FIG. 2 and for generating an output signals indicating the temperature difference between the probes and the absolute temperature of one of the probes of the calorimetric sensor of FIG. 2.

To provide for energization of the sensing elements 40 and 42, and to provide for analysis of the exhaust gas information transduced by the sensors 40 and 42, the circuit of FIG. 3 is provided as but one example of how such energization and analysis may be carried out in accord with this invention. Through ordinary skill in circuit design, one may provide for the aspects of this invention which include a pulsed energization of the sensing elements 40 and 42 to avoid self-heating of the elements yet to facilitate reading of the elements with sense signals characterized by a beneficial signal to noise ratio.

Specifically, the circuitry for the present embodiment as illustrated in FIG. 3 includes the sensor drive circuit 26 of FIG. 1 having a timer circuit 60 to which is applied an ignition voltage Vign, such as a regulated twelve volt signal. The timer circuitry generally consists of the conventional 555 timer configured to output a square wave clock signal CK at a frequency of approximately 167 Hz. The output clock signal CK is applied to a pulse generator 62 which may include a simple, commercially available 8-bit counter such as a conventional 4024 counter generally known in the art. Interface circuitry, such as simple logic circuitry may likewise be included as part of the pulse generator 62, as will be further described. The pulse generator provides, in this embodiment, output signals P1 and P2. The output signal P1 is preferably a short duration pulse, such as about a five millisecond pulse, occurring about event 250 milliseconds while ignition power is applied to the PCM 14 (FIG. 1). P1 is the pulse used to indicate the short period of energization of the sensing elements 40 and 42 during which the resistance of the elements may be read while minimizing self-heating of the elements in accord with this invention. Such a pulse P1 may be established through conventional interface circuitry applied to a portion of the eight parallel output signals available with the standard eight bit counter included with the pulse generator 62.

For example, such a pulse P1 may be established by exclusive OR'ing the two least significant bits of the parallel counter output and AND'ing the exclusive OR output with the most significant counter output bit, and providing the AND gate output as the signal P1. Output pulse P2 is a pulse of short duration, such as about 2–3 millisecond duration, with a rising edge occurring substantially at the time of the rising edge of pulse P1, but with a falling edge occurring well before the falling edge of pulse P1. Like the signal P1, pulse P2 should be set up to occur about every 250 milliseconds while ignition power is applied to the PCM 14 (FIG. 1).

The pulse P2 is used to indicate a sensor output signal sampling period, and is synchronized with signal P1 to ensure valid sensing data is read and processed by the circuitry of FIG. 3. To provide for the pulse P2, the least significant and most significant counter bits may be logical AND'ed together and the AND gate output provided as P2. To provide for counter reset, the two least significant, and the most significant bits of the counter may be logical AND'ed together and the output of the three input AND gate or its equivalent applied to a standard reset pin of the counter.

The output pulse signal P1 is applied to a constant current supply circuit 64 of conventional design set up to drive a constant current signal through the catalyzed element 40 and the inert or non-catalyzed element 42. The constant current supply 64 may be any simple conventional current source which rapidly supplies a substantially constant current through the series connection of the sensing elements 40 and 42 while the pulse P1 is high. In this embodiment, the current i supplied by the supply 64 should be about two milliamperes constant while P1 is high. The signal i will pass across the sensing element 40 and then to the sensing element 42 and then to a ground reference. In accord with the critical feature of this invention, the signal i of short duration provides sufficient current across the sensing elements 40 and 42 so that the resistance of the elements may be measured, while minimizing self heating of the elements. Sensor self-heating is not required to elevate the catalyst of sensing element 40 to light-off, as heat energy transferred from engine exhaust gas to the catalyst is sufficient to rapidly elevate the catalyst temperature to light-off, as described. By applying the short pulse of current i through the catalyzed and inert elements 40 and 42, respectively, convective losses are substantially eliminated since the elements are maintained at the temperature of the engine exhaust gas. This provides that the sensor output of sensing elements 40 and 42 will only be a function of the catalytic activity of element 40 and the heat transfer properties of element 40. This further provides that the temperature information provided by the sensing element 42 may be used for a measure of engine exhaust gas temperature, as the temperature of the sensing element 42 is substantially solely a function of exhaust gas temperature. Furthermore, in accord with an important feature of this invention, the current pulse of short duration allows for higher amplitude voltage to be applied across the sensing elements 40 and 42 without self heating. Such higher amplitude voltage signals increase sensor signal-to-noise ratio improving distinguishably of the sensor output signals. Such an aspect is particularly important in automotive applications in which signal noise is abundant.

In this embodiment, combustible gas concentration is expressed as a function of difference in resistance $\Delta R$ between the catalyzed and non-catalyzed elements 40 sensor 36 respectively of the sensor 36. The resistance difference $\Delta R$ indicates the temperature difference between the elements 40 and 42, and thus indicates the degree of catalytic activity occurring at the surface of the catalyzed element 40. As the sensing elements 40 and 42 are not self-heated in accord with this invention, the sensing element 42 will be substantially at exhaust gas temperature, and catalyzed element 40 will be elevated to a temperature above the exhaust gas temperature, once the catalyst is elevated to light-off. The temperature elevation is caused by the exothermic oxidation reaction occurring between the catalyst and the combustible elements of CO and HC that may be present in the engine exhaust gas passing by the catalyst. The concentration of CO and, at least at high exhaust gas temperatures HC, is directly related to the amount of oxidation taking place and thus to the amount of energy transferred to the sensing element 40, so that the elevation in temperature of the sensing element 40 above that of the noncatalyzed element 42 indicates such concentration.

To provide a measure of the difference in temperature, the $\Delta R$ value is generated as follows. Under Ohm's law, the resistance of the catalyzed element 40 may be expressed as $$(V_t - V_n)/i$$

in which Vt is the voltage at the constant current supply 64 output, Vn is the voltage at the node formed between the sensing elements 40 and 42, and i is the constant current applied to the sensing elements by the supply 64. Likewise, the resistance of the non-catalyzed element 42 may be expressed under Ohm's law as $$V_n/i.$$

The difference in resistance Rc−Rn, indicating the concentration of combustible elements in the engine exhaust gas, may therefore be represented as $$(V_t - V_n)/i - V_n/i$$

which may further be reduced to $$(V_t - 2 * V_n)/i.$$

This representation is provided through the signal analysis circuit 16 of FIG. 3 as follows. The output of amplifier 66 provides the value 2*Vn. The difference value Vt−2*Vn is provided by the differential amplifier 68. The current i is known and substantially constant, and is applied by the PCM 14 to form the quotient (Vt −2*Vn)/i.

More specifically, the signal analysis circuit functions as follows. The voltage Vn across the non-catalyzed element 42 is applied to a standard amplifier 66, such as a simple operational amplifier-based linear amplifier circuit having a gain of approximately two. The output of the amplifier 66 and the voltage across catalyzed element 40 are applied to a differential amplifier 68. The differential amplifier may be any of the significant number of commercially available two-stage amplifier configurations performing a precision gain and difference function about a fixed reference slightly above the ground reference. The differential amplifier 68 outputs a signal Vo which may be expressed as $$Vo = K * (V_t - V_n) + V_{ref}$$

in which Vref is a predetermined, fixed reference voltage which may be set through standard voltage divider circuitry to be a voltage slightly greater than the ground reference voltage. The gain K is a fixed gain value set to amplify the difference between the voltage across the catalyzed element 40 and the non-catalyzed element 42, such as a gain of approximately ten to eleven in this embodiment. The differential amplifier output signal Vo is applied as the data input to sample and hold circuitry S/H 70 which may be configured as a standard LF198 sample and hold circuit. The control input to the S/H circuit 70 is the described pulse signal P2 generated by pulse generator 62. The sample and hold circuit 70 provides for a periodic sampling of Vo for application to the PCM 14 for engine control and diagnostic as will be described. When the pulse generator output signal P2 is high, the data input to S/H 70 is passed through to a gain and offset stage 72 for adapting the signal for interpretation by the standard input circuitry of PCM 14. For example, the gain and offset applied at the stage 72 should be set up so that the output signal Vout from the stage 72 to the PCM 14 ranges from zero to five volts, to maximize signal resolution. A standard analog to digital converter (not shown) may be provided as PCM 14 input circuitry to convert Vout over the five volt range to a digital equivalent. For a converter having a range of zero to five volts, Vout should vary over as much of that five volt range as can reasonably be provided.

To provide for engine exhaust gas temperature sensing, output signal P2 of pulse generator 62 is provided to standard sample and hold S/H circuit 74 as a control input. The circuit 74 may substantially be a standard LF198 sample and hold circuit element with pulse signal P2 applied as a control input and the voltage Vn across the non-catalyzed element 42 applied as the data input. Accordingly, at the rising edge of pulse generator output signal P2 and for the duration of P2, the sample and hold circuit 74 will pass the voltage Vn through to a gain and offset stage 76 so that a valid 0 to 5 volt signal may be generated and applied as output signal Vtemp to the PCM 14. The gain and offset stage 76 may have any gain or offset that is required to condition the output voltage across the non-catalyzed element 42 as necessary for maximum resolution conversion in this embodiment by the standard input circuitry of the PCM 14.

Figure 4:
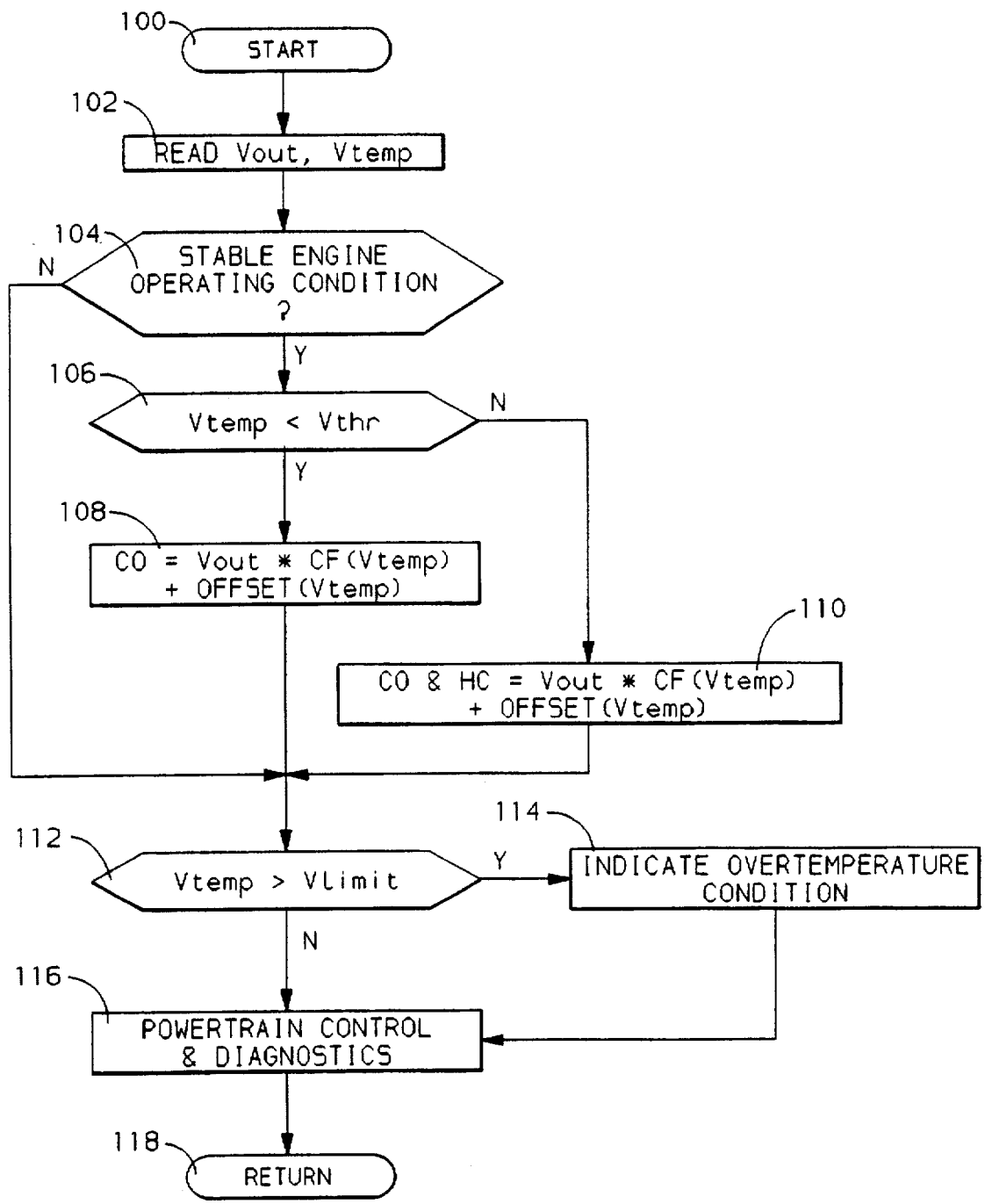
FIG. 4 is a flow of controller operations for transforming the output signals provided by the circuitry of FIG. 3 into emissions information that may be applied in powertrain control and diagnostics.

Turning to FIG. 4, a series of PCM operations are illustrated to provide for receiving and processing of the signal Vout and Vtemp as generated through the described operations of the circuitry schematically illustrated in FIG. 3. The operations of FIG. 4 may be periodically executed while the PCM 14 of FIG. 1 is operating such as while an ignition power source is manually applied to the PCM 14. For example, the operations of FIG. 4 may be executed once following each falling edge of pulse signal P1 of FIG. 3 so that for each sampling of signals Vout and Vtemp through the described functioning of the circuitry of FIG. 3, PCM operations may be provided to read Vout and Vtemp and to process such voltage signals in accord with this invention. Alternatively, the operations of FIG. 4 may be periodically executed at a predetermined rate or upon occurrence of a predetermined event providing, however, at a minimum, that the operations of FIG. 4 are executed at a high enough frequency to provide sufficiently up to date information indicating the emissions levels of the automotive vehicle internal combustion engine and the engine exhaust gas temperature for the application intended for such information.

Specifically, upon completion of a predetermined time period or following occurrence of a predetermined event, such as following each falling edge of pulse generator output signal P1 of FIG. 3, the routine of FIG. 4 is executed starting at step 100 and proceeding to a step 102 to read the input signals Vout and Vtemp such as may be stored at addresses in PCM memory corresponding to input circuitry such as analog to digital convertor circuitry as is generally understood in the art. At the step 102, the determination of a quotient indicating the value ΔR may be provided by dividing Vout by a constant representing the current i which, as described will yield a value indicating the resistance difference ΔR After reading the voltage values at the step 102, and after adjusting, if desired Vout to reflect the value ΔR, the current engine operating condition is analyzed at a next step 104 to determine if it may be characterized as a stable operating condition. In this embodiment, an engine operating condition is stable if a series of engine parameters are stable. Such parameters include engine coolant temperature TEMP, engine intake manifold absolute pressure MAP, vehicle speed Vspd, engine intake valve position TP. Such parameters may be monitored by periodically storing their values and differentiating such stored values to determine the time rate of variation in such parameters. Such time rates of variation may be compared to calibrated threshold time rates of variation at the step 104 to determine if the engine operating condition is stable. For example, if any of the time rates of variation of the described engine parameters exceeds its corresponding threshold time rate of variation value, then the engine operating condition may be assumed to not be sufficiently stable to support an acceptably accurate analysis of engine exhaust gas constituent elements in accord with this embodiment. If the engine is assumed to not be sufficiently stable at this step 104, the routine proceeds to a step 112, to be described. However, at the step 104, if the time rate of variation of the described engine parameters are all less than the corresponding threshold time rates of variation, the routine proceeds to analyze engine emissions in accord with this invention by first comparing the value Vtemp indicating exhaust gas temperature to a threshold voltage Vthr at a step 106. Vthr represents a calibrated exhaust gas temperature threshold below which the calorimetric sensor of the present embodiment is substantially insensitive to variation in HC concentration. Therefore, only the concentration of CO may be detected when Vtemp is less than Vthr, which is calibrated to a value representing about 390 degrees Celsius in this embodiment.

Figure 5:
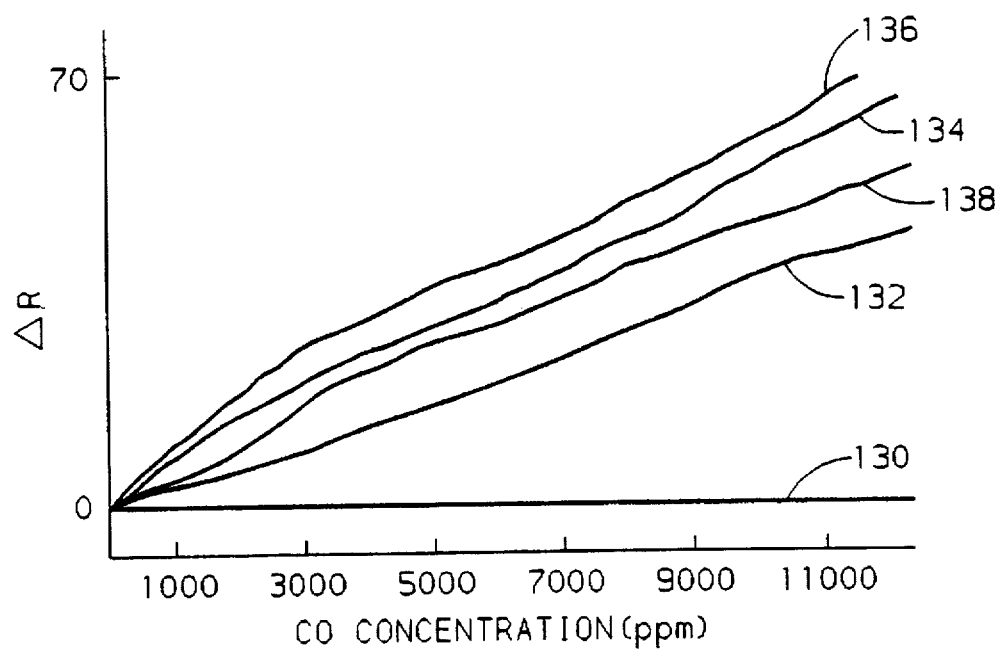
FIGS. 5 and 6 illustrate representative relationships between the sensor output signals and engine emissions.
Figure 6:
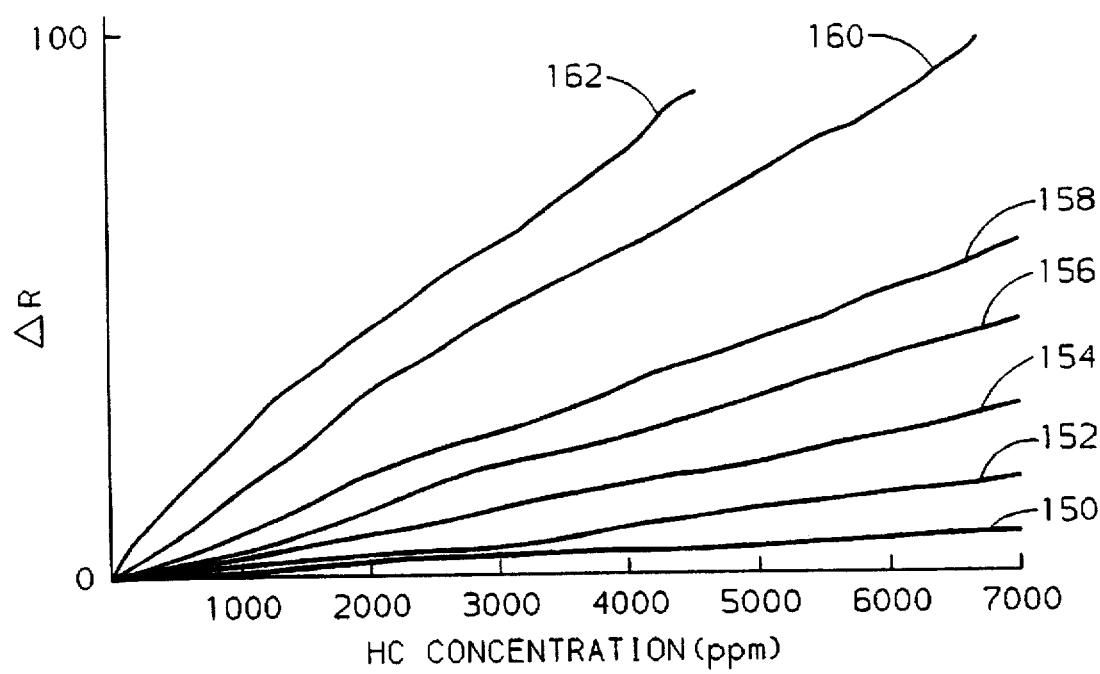

FIGS. 5 and 6 are provided to illustrate the relationship between ΔR of the sensing elements 40 and 42 of FIG. 3, and the concentration of CO and HC over a range of exhaust gas temperatures. Each of the family of curves of FIGS. 5 and 6 corresponds to a different exhaust gas temperature, evidencing the importance of including information on exhaust gas temperature in the determination of CO and HC concentration from a measured ΔR value. For example, curve 130 of FIG. 5 illustrates that for any of a large number of CO concentrations the ΔR value will be substantially zero for an exhaust gas temperature of about 200° C. With increasing temperature, the ΔR value will increase substantially in a linear fashion for variations in CO concentration. For example, curve 132 illustrates the relationship of ΔR to CO concentration at an exhaust gas temperature of about 250° C. Curve 134 illustrates the relationship for an exhaust gas temperature of about 320° C., curve 136 illustrates the relationship for a temperature of about 360° C., and curve 138 illustrates the relationship for an exhaust gas temperature of about 430° C. To provide for accurate CO concentration measurement using the ΔR value yielded by the described circuitry of FIG. 3, an adjustment must be made for exhaust gas temperature both in offset and in slope of the function relating CO concentration to ΔR. Accordingly, and using the information represented by the measurements that establish the family of curves of FIG. 5, an offset and a gain may be determined as a function of Vtemp which represents exhaust gas temperature, so that for a given ΔR value the proper CO concentration may be derived. Such gain and offset variation may be stored in the form of a conventional lookup table in non-volatile PCM 14 memory as a predetermined function of Vtemp, wherein the table entries of gain and offset may be determined through a conventional calibration process as a function of exhaust gas temperature. FIG. 5 generally illustrates the information required to generate, through the exercise of ordinary skill in the art, the table entries of gain and offset as a function of exhaust gas temperature.

Likewise, the family of curves of FIG. 6 represents the relationship between a measured ΔR value and hydrocarbon HC concentration in the engine exhaust gas over a range of exhaust gas temperatures. For example, curve 150 represents the relationship between ΔR and HC concentration in the exhaust gas at a temperature of about 300°. Likewise for a temperature of about 340° C., the relationship between ΔR and HC concentration is illustrated by curve 152. Curve 154 illustrates the relationship at about 385° C., curve 156 illustrates the relationship at a temperature of about 430° C., curve 158 represents the relationship at about 450° C., curve 160 represents the relationship at about 470° C., and curve 162 represents the relationship measured at 490° C. As illustrated by curves 150–154 of FIG. 6, the ΔR value is substantially insensitive to significant changes in HC concentration for exhaust gas temperature below about 390° C. Accordingly, when Vtemp indicates an exhaust gas temperature below such a calibrated temperature, any ΔR magnitude is likely to be due to oxidation of CO at the catalyst surface of element 40 (FIG. 3) and not to oxidation of HC. Accordingly, and as described, if Vtemp indicates a temperature below Vthr of about 390 degrees in this embodiment, only CO concentration will be assumed to be indicated by the value ΔR Returning to FIG. 4, if Vtemp is less than Vthr at the step 106, a step 108 is executed to calculate the carbon monoxide concentration CO as follows:

CO=Vout * CF(Vtemp)+OFFSET(Vtemp)

in which CF(Vtemp) is referenced, such as from a conventional lookup table in non-volatile PCM memory, as a calibrated function of Vtemp, as described, and OFFSET (Vtemp) is referenced, such as from a conventional lookup table in non-volatile PCM memory, as a calibrated function of Vtemp, as described. These referenced values are provided to account for any change in slope or any change in offset over a range of engine exhaust gas temperatures in the relationship between ΔR and CO concentration, for example as illustrated in the described FIG. 5. After determining the CO concentration at the step 108, a next step 112 is executed, to be described.

Returning to the step 106, if Vtemp is not less than Vthr, then both HC and CO may be detected by the ΔR value represented as Vout, and a step 110 is next executed to calculate the CO and HC concentration as follows:

[CO,HC]=Vout * CF(Vtemp)+OFFSET(Vtemp)

in which CF(Vtemp) and OFFSET(Vtemp) are again referenced from a calibrated function of the degree of slope change and shift in the CO and HC concentration relationship to ΔR. FIGS. 5 and 6 illustrate such slope change and shift that is to be compensated through the calibrated functions.

After determining the CO and HC concentrations at the step 110, or the CO concentration at the step 108, or if a stable engine operating condition was not detected at the step 104, a next step 112 is executed to compare the engine exhaust gas temperature as indicated by Vtemp to a limit value Vlimit. The temperature limit value Vlimit may be determined through a conventional calibration process as the voltage corresponding to an exhaust gas temperature that is the maximum fault free exhaust gas temperature for the powertrain to which the principles of this invention are applied. For example, Vlimit may be established at a level necessary to diagnose an overtemperature condition in the engine exhaust gas, such as a condition that may result in damage to conventional exhaust system components included in the system to which this invention is applied. In this embodiment, Vlimit is set to correspond to a temperature of about 900 degrees Celsius. If the exhaust gas temperature as indicated by Vtemp exceeds Vlimit, then an overtemperature condition exists that may be indicated so that corrective action may be taken by the vehicle operator, such as by reducing the operating level of the powertrain or by servicing an appropriate powertrain component, if necessary.

Specifically, at the step 112, if Vtemp exceeds Vlimit an over temperature is indicated at a step 114 such as by storing an error code in powertrain control module memory, and by illuminating a display device visible to the vehicle operator. Next, or if the overtemperature condition was not detected at the step 112, any conventional powertrain control and diagnostics that may be executed at the iteration rate of the routine of FIG. 4 may be carried out at a next step 116. Such control and diagnostic operations may include conventional operations relying on the detected concentration of CO and HC as provided in accord with the operations of the routine of FIG. 4 including emissions control and diagnostics functions as well as powertrain control functions, for example that are required to drive the concentration of CO and HC in the engine exhaust gas to acceptable levels in accord with generally understood emissions control performance guidelines. After executing any conventional powertrain control and diagnostic operations that may be required at the step 116, including operations to store and generally make available the concentration information derived through the operations of FIG. 4 for use generally by the powertrain control module 14 of FIG. 1, the routine of FIG. 4 proceeds to a step 118 to return to any prior operations that were ongoing at the time the routine was initiated.

In accord with a further aspect of this invention, the inert (non-catalyzed) element, such as element 42 of FIG. 2, may be used for measuring engine exhaust gas flow rate and the flow rate used to compensate for any flow rate-based variations in heat transfer properties of the elements. For example, at the described step 116 of FIG. 4, a routine may be executed to provide for a short period of self-heating of the inert element 42 (FIG. 2), such as by applying a current pulse across the element 42, such pulse having a predetermined, calibratable duration that is significantly longer than the duration of the pulse of the preferred embodiment. Following the self-heating pulse, the temperature of the inert element 42 should be periodically sampled while it cools. The time rate of change of element temperature may thus be established and, with the exhaust gas temperature indicated by Vtemp that was read at the step 102, the flow rate of engine exhaust gas may be determined, as a predetermined function generally understood in the art of the rate of change in temperature and the temperature indicated by Vtemp, as well as of the physical characteristics of the system, which may be measured during a conventional calibration process and stored in controller memory, such as read only memory. The determined flow rate may then be used for a variety of control and diagnostic purposes, including compensating for any flow rate-based variations in heat transfer properties of the elements. Specifically, a heat transfer property correction value may be referenced from a stored schedule using the measured flow rate, and the correction value used in determining subsequent concentration values.

The preferred embodiment for the purpose of explaining this invention is not to be taken as limiting or restricting this invention since many modifications may be made through the exercise of ordinary skill in the art without departing from the scope of the invention.

The embodiments of the invention in which a property or privilege is claimed are described as follows:

1. A method of determining the concentration of combustible engine exhaust gas elements, comprising the steps of:
   exposing a catalyzed temperature sensitive element which is coated with a catalyst and an inert temperature sensitive element to a flow of internal combustion engine exhaust gas;
   applying a pulse of electrical current through the catalyzed and the inert elements;
   determining the electrical resistance of the catalyzed and of the inert elements;
   generating signals representing the concentration of combustible engine exhaust gas elements as a predetermined function of the determined electrical resistance.

2. The method of claim 1, wherein the determining step further comprises the steps of:
   sampling the voltage across the catalyzed and across the inert elements while the pulse of electrical current is being applied through the catalyzed and the inert elements; and
   determining the electrical resistance of the catalyzed and of the inert elements as a predetermined function of the current pulse applied to the elements and of the voltage sampled across the respective catalyzed and inert elements.

3. The method of claim 1, wherein the current pulse has a predetermined pulsewidth of short duration such that substantially no additional heating of the catalyzed and inert elements results from application of the current pulse at the applying step.

4. The method of claim 1, further providing for exhaust gas temperature sensing, further comprising the step of:

determining engine exhaust gas temperature as a predetermined function of the electrical resistance of the inert element.

5. The method of claim 4, wherein the generating step generates signals representing the concentration of combustible engine exhaust gas elements as a predetermined function of the determined electrical resistance and of the determined engine exhaust gas temperature.

6. The method of claim 1, further for determining engine exhaust gas flow rate, further comprising the steps of:

providing for self-heating of the inert element by applying current to the inert element for a predetermined period of time sufficient to increase the temperature of the inert element;

following the predetermined period of time, periodically determining the electrical resistance of the inert element by (a) applying a pulse of electrical current through the inert element, (b) measuring the voltage drop across the inert element while the pulse of electrical current is being applied to the inert element, and (c) determining the electrical resistance of the inert element as a predetermined function of the current pulse applied through the inert element and of the measured voltage drop;

estimating a rate of change of temperature of the inert element as a predetermined function of the periodically determined resistance; and calculating exhaust gas flow rate as a predetermined function of the estimated rate of change.

7. An apparatus for sensing concentration of combustible elements in internal combustion engine exhaust gas, comprising:

a first and a second temperature sensitive elements exposed to internal combustion engine exhaust gas, the first element being coated with a catalyst so as to catalytically react with the combustible elements in the engine exhaust gas, wherein energy generated in the catalytic reaction elevates the temperature of the first element above the temperature of the second element;

a current pulse generating circuit for generating a current pulse and for applying the current pulse through the first and second temperature sensitive elements;

a voltage sampling circuit for sampling voltages across the first and the second temperature sensitive elements while the current pulse is passing through the elements;

concentration determining means for determining the concentration of the combustible elements in the engine exhaust gas as a predetermined function of the sampled voltages.

8. The apparatus of claim 7, wherein the concentration determining means comprises:

a difference determining circuit for generating a resistance difference signal indicative of a resistance difference between the first and second temperature sensitive elements as a predetermined function of the sampled voltages; and a controller comprising (a) input circuitry for receiving the generated resistance difference signal, and (b) a central processing unit for generating concentration values as a predetermined function of the received signal.

9. The apparatus of claim 8, wherein the controller further comprises:

a read only memory unit storing predetermined schedules of concentration values as a function of resistance difference signal values; and wherein the central processing unit comprises arithmetic logic circuitry for referencingfrom read only memory the concentration value corresponding to the received resistance difference signal.

10. The apparatus of claim 7, wherein the current pulse is of a predetermined duration that is sufficiently short that substantially no element heating occurs in response to application of the pulse to the elements.

11. The apparatus of claim 7, further for sensing engine exhaust gas temperature, further comprising:

temperature determining means for determining the temperature of the engine exhaust gas as a predetermined function of the sampled voltage across the second temperature sensitive element.

12. The apparatus of claim 11, wherein the temperature determining means further comprises:

input circuitry for receiving the sampled voltage across the second temperature sensitive element; and arithmetic logic circuitry for generating a value representing exhaust gas temperature as a predetermined function of the received signal.

* * * * *